US00PP35438P2

(12) United States Plant Patent
Hansen

(10) Patent No.: US PP35,438 P2
(45) Date of Patent: Oct. 24, 2023

(54) ***BUDDLEIA* PLANT NAMED 'PINK CASCADE II'**

(50) Latin Name: *Buddleia davidii*
Varietal Denomination: Pink Cascade II

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 14 days.

(21) Appl. No.: 17/803,928

(22) Filed: Jan. 26, 2023

(51) Int. Cl.
*A01H 5/00* (2018.01)
*A01H 6/00* (2018.01)

(52) U.S. Cl.
USPC ..... Plt./242

(58) Field of Classification Search
USPC ..... Plt./226, 242
See application file for complete search history.

*Primary Examiner* — Karen M Redden

(57) ABSTRACT

The new and distinct plant of *Buddleia* 'Pink Cascade II' is a rounded-mounded, multi-stemmed, winter-hardy butterfly bush with very long, broad, slightly pendulous flowering thyrse producing a waterfall effect over a long season beginning mid-summer with sweetly fragrant flowers of pinkish petals that are attractively offset by dark green foliage with silvery undersides. No seed has been observed on this plant and it is presumed to be sterile. The new plant is valuable for landscaping en masse, as an accent or as a potted specimen.

1 Drawing Sheet

Botanical classification: *Buddleia davidii.*
Variety denomination: 'Pink Cascade II'.

STATEMENT REGARDING PRIOR DISCLOSURES UNDER 37 CFR 1.77(b)(6)

The first non-enabling information of the claimed plant, in the form of a photograph and brief description was on a website operated by Walters Gardens, Inc. on Feb. 1, 2022. *Buddleia* 'Pink Cascade II' was later listed with a photograph and brief description in the "Walters Gardens 2022-2023 Catalog" distributed initially on Jun. 8, 2022. The claimed plant was first sold to Plant Delights Nursery, Inc. on Sep. 19, 2022 by Walters Gardens, Inc., who obtained the plant and all information relating thereto, from the inventor. No plants of *Buddleia* 'Pink Cascade II' have been sold in this country or anywhere in the world, nor has any disclosure of the new plant been made, more than one year prior to the filing date of this application, and such sale or disclosure within one year was either derived directly or indirectly from the inventor.

BACKGROUND OF THE PLANT

The present invention relates to the new and distinct butterfly bush plant of the Scrophulariaceae family, *Buddleia* 'Pink Cascade II' hybridized by the inventor in the summer of 2018 at a wholesale perennial nursery in Zeeland, Mich., USA. 'Pink Cascade II' is the result of an ongoing breeding program conducted by the inventor. The goals for this program have been to produce improved, garden-worthy plants for the ornamental plant market. The new plant was the result of a single seedling selection from a cross between the unreleased proprietary hybrid 17-22-1 (not patented) as the female or seed parent and the male parent was an unreleased proprietary hybrid sibling with the in-house breeder code 17-22-2 (not patented). The new plant was assigned the breeder code 18-15-4 to identify it during the evaluation trials.

*Buddleia* 'Pink Cascade II' was first asexually propagated from a single select seedling in 2020 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

In comparison to the new plant the female parent has a pendulous lilac-colored flowers and is upright in habit. The male plant has shorter, upright habit with lilac-purple-colored flowers.

The nearest comparison plants known to the inventor are *Buddleia* 'Grand Cascade' U.S. Plant Pat. No. 30,868, 'Lavender Cascade' U.S. Plant Pat. No. 30,635, 'Lilac Cascade' U.S. Plant Pat. No. 33,851, 'Pink Cascade' U.S. Plant Pat. No. 30,711, 'Pink Delight' (not patented), 'Pink Pagoda' U.S. Plant Pat. No. 23,214, and 'Wisteria Lane' U.S. Plant Pat. No. 27,833.

'Grand Cascade' has a larger habit and the flowers are light lavender-purple. Lavender Cascade' has a larger habit and the flowers are a soft lavender-purple. 'Lilac Cascade' has a slightly larger habit and the flowers are a light purple. 'Pink Cascade' has a slightly larger habit and the flowers are a deeper apple blossom pink. 'Pink Delight' has a slightly larger habit with smaller and more upright thyrse of deeper pink flowers. 'Pink Pagoda' is shorter and narrower in habit with more open and smaller thyrse having flowers of a deeper more medium pink color. 'Wisteria Lane' is shorter in habit with smaller thyrse and the branches are more drooping instead of mainly the thyrse drooping and the petals are light purple.

*Buddleia* 'Pink Cascade II' is a unique winter-hardy butterfly bush different from all other *Buddleia* cultivars known to the inventor based on the following combined repeatedly observed distinguishing traits:

1. Winter-hardy butterfly bush shrub, with multiple-stemmed, well-branched, rounded, waterfall-type arching, mounded habit;
2. Long, broad, many-flowered, elongated, and slightly-drooping thyrse flowering beginning mid-summer until frost;
3. Flowers with pinkish petals;
4. Lanceolate foliage of dark green with silvery undersides
5. No seed observed and presumed to be sterile.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
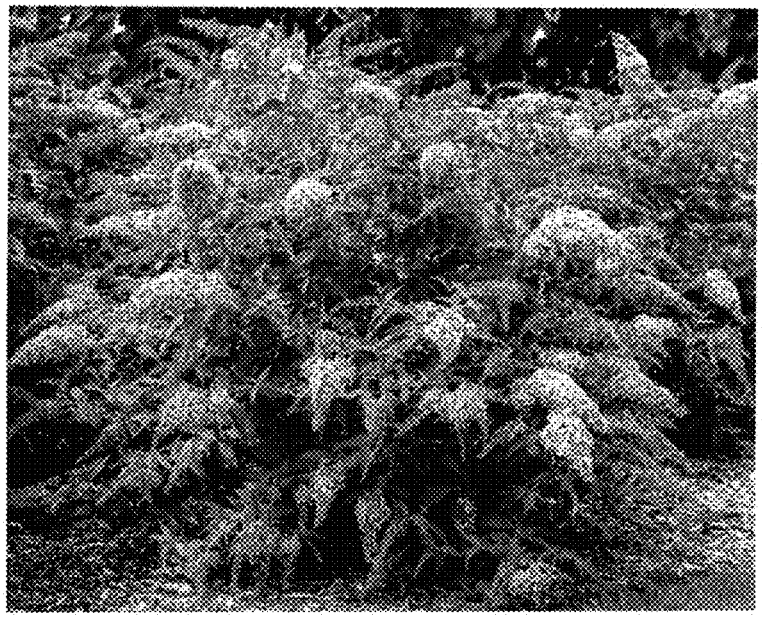
FIG. 1 shows the habit of a three-year-old plant in mid-season flowering.
Figure 2:
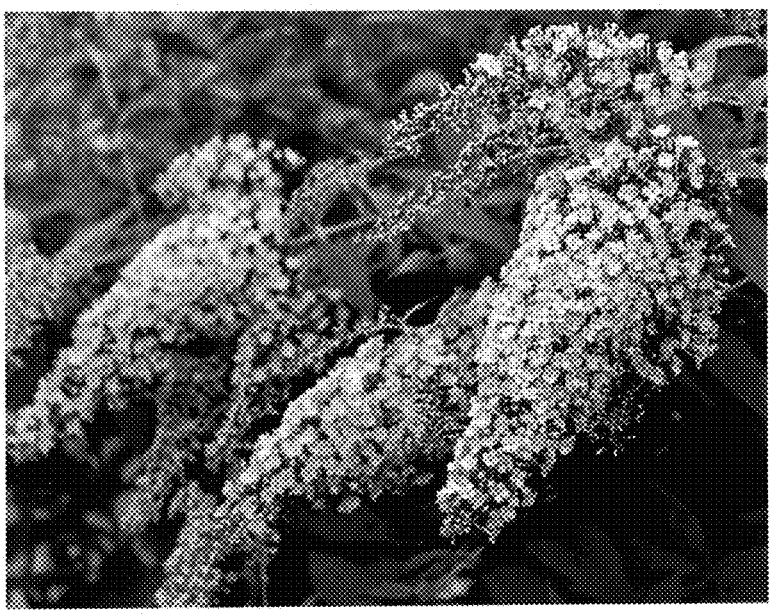
FIG. 2 shows a close-up of the inflorescence with flowers and buds.

The following descriptions and color references are based on the 2015 edition of The Royal Horticultural Society Colour Chart except where common dictionary terms are used. The new plant, *Buddleia* 'Pink Cascade II', has not been observed under all possible environments. The phenotype may vary slightly with different environmental conditions, such as temperature, light, fertility, moisture, and maturity levels, but without any change in the genotype. The following observations and size descriptions are of a three-year-old plant in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 17-22-1 (not patented) as the female or seed patent; the male or pollen parent was an unreleased proprietary hybrid known as 17-22-2.

Propagation:

*Method.*—Softwood shoot cuttings.

*Time to initiate roots from tissue, culture.*—About two weeks.

*Rooting habit.*—Normal, dense and branching, developing thick at base to about 1.5 cm diameter.

*Root color.*—Creamy white between RHS 159A and lighter than RHS 159 D depending on soil type.

*Crop time.*—Under normal summer growing conditions 12 to 15 weeks to flower in a four-liter container from cutting. Plant vigor is very good.

Plant description:

*Plant shape and habit.*—Winter-hardy, herbaceous to semi-woody, well-branched shrub with about 20 thick upright and branched main stems producing a rounded mound, to about 125 cm tall and about 210 cm wide.

*Stem.*—Terete and woody in lower portion, with exfoliating bark; younger upper portion tomentose to tomentulose; strong and flexible, arching or drooping especially in terminal thyrse; average about 110 cm tall from soil line to just below terminal flowers, and about 18 mm diameter at the base; about 26 branches per main stem before distal flowers in upper 13 nodes, extending at about 45° angle from main stem.

*Stem color.*—Young distal portion just below flowers nearest RHS 146D with variably blushing of nearest RHS 187B of great concentration with higher light exposure; basal 15 cm nearest RHS N199C and RHS 165B with striations nearest RHS 199D.

*Internode.*—About 18 nodes per main stem below terminal thyrse, average internode length about 5 cm on unpinched plant; upper internodes slightly more elongated than lower internodes.

Foliage description: Opposite; lanceolate; decussate; serrate with about six teeth per cm, teeth about 1 mm long and 1.5 mm wide; young expanding leaves glabrous adaxial, tomentulose abaxial; cuneate base and narrowly acute apex; no foliar fragrance detected.

*Leaf blade size.*—Up to about 135 mm long and about 43 mm wide, average about 103 mm long and about 25 mm wide; becoming smaller in distal portion of stem.

*Foliage color.*—Young expanding leaf adaxial nearest RHS 146B, young expanding abaxial nearest RHS 191C; mature leaves adaxial nearest RHS NN137A, mature abaxial nearest RHS 194B.

*Veins.*—Pinnate; adaxial glabrous, slightly impressed; abaxial costate, tomentulose.

*Vein color.*—Young adaxial midrib and secondary veins nearest RHS 160D, young abaxial midrib nearest RHS 195C and secondary veins nearest RHS 191C; mature adaxial midrib nearest RHS 160B and secondary veins nearest RHS NN13B, abaxial midrib and secondary veins nearest RHS 194D.

*Petioles.*—Slightly applanate; adaxial glabrous; abaxial tomentulose; to about 10 mm long and 2.5 mm wide.

*Petiole color.*—Adaxial nearest RHS 147C; abaxial between RHS 148C and RHS 195B.

*Inflorescence description.*—Glomerate thyrse consisting of about 1,500 to 3,000 self-cleaning salverform flowers; to about 33 cm long and 13 cm wide at base; average about 30 cm long and 10 cm wide; beginning in mid-July and continuing until frost in Michigan; thyrse effective for about three weeks.

*Inflorescence attitude.*—Slightly drooping.

*Flower buds one day prior to opening.*—Elongated clavate, apex rounded; glabrous; about 14 mm long, club portion about 3 mm diameter, tube about 1 mm diameter and about 11 mm long.

*Flower bud color.*—Nearest RHS 72C in club portion, distal corolla tube portion nearest RHS N170D, middle exposed corolla tube portion nearest RHS 58A; calyx nearest RHS 187A in higher light exposure and nearest RHS 146B where protected from high light exposure.

*Calyx.*—Campanulate; to about 3 mm long and 1 mm wide at apex.

*Sepals.*—Four; adpressed to corolla tube; acute apex; glabrous adaxial and micro-puberulent abaxial; margin entire; fused in about the basal 2 mm and split in about the terminal 1 mm, individually about 0.7 mm wide at fusion.

*Sepal color.*—Nearest RHS 187A in high light exposure and nearest RHS 146B low light exposure.

*Flowers.*—Salverform; actinomorphic; perfect; to about 13 mm long and an abruptly applanate face 9 mm wide; with straight terete corolla tube about 11 mm long and 1.5 mm diameter near face and 1 mm diameter at base; attitude outward from thyrse center; remaining on the thyrse and effective for about five to seven days.

*Flowers fragrance.*—Pleasantly and distinctly sweet.

*Petals.*—Typically four; glabrous adaxial blades and tube, and abaxial; puberulent center abaxial tube; blade rounded with crenate margin; apex rounded; blade to about 4.5 mm across and about 4 mm long from throat to apex.

*Petal color.*—Variable; upon initial opening adaxial face between RHS 72C and RHS 72D, nearer RHS 72D with warmer growing conditions, center eye nearest RHS 14A, inner corolla tube nearest RHS 17B, and basal 2 mm translucent to nearest RHS NN155A; upon initial opening abaxial face between RHS N74D and RHS NN74D in higher growing temperatures and between RHS N74 C and RHS N74D in cooler growing temperatures, distal portion of corolla tube nearest RHS 35D, middle portion of tube between RHS 184C and RHS 184B, basal 1 to 2 mm translucent to nearest RHS NN155A; when fully open adaxial blade face nearest RHS NN74D, eye nearest RHS 17B, distal and middle corolla tube nearest RHS N25D, basal 2 mm translucent to nearest RHS 155D; when fully open abaxial petal blades nearest RHS NN74D, distal corolla tube between RHS N170D and RHS 179D, middle corolla tube between RHS 181B and RHS 180B, basal 2 mm RHS NN155D.

*Gynoecium.*—Pistil: one; about 5 mm long. Style: glabrous, glutinous, ellipsoidal; about 1.5 mm long and about 0.3 mm diameter; color nearest RHS 145D. Stigma: narrow ellipsoidal, lustrous; about 1.5 mm long and about 0.3 mm in diameter; color nearest RHS 145A. Ovary: superior; ellipsoidal; rounded base and rounded apex; about 2 mm tall and 1 mm across at base; color nearest RHS 144A.

*Androecium.*—Four; vestigial. Filaments: short or less than 0.5 mm long and less than 0.1 mm diameter; adnate to the middle of adaxial corolla tube about 6 mm from base; color nearest RHS NN155D. Anthers: typically, four; ellipsoidal; basifixed; about 1 mm long and 0.3 mm wide; color nearest RHS 162B. Pollen: not observed.

*Pedicel.*—Short; cylindrical; tomentulose; about 2.0 mm long and about 0.5 mm diameter; color nearest RHS NN137D highly blushed in high light-exposed portions with nearest RHS 187A.

*Peduncle.*—Quadrangular; tomentulose, flexible and strong; to about 41 cm long, and about 4 mm across at base below flowers.

*Peduncle color.*—Between RHS 147B and RHS 146B, variably blushed with nearest RHS 183B in greater intensity with higher light exposure.

*Fruit and seed.*—Not observed to date despite growing in trials with large number of pollinators where seed set is common; presumed to be sterile.

Disease resistance: Typical resistance has been noted to deer browsing; other pest and disease resistance beyond that common to butterfly bush cultivars has not been observed.

Growth: The plant grows best with plenty of moisture and adequate drainage but is able to tolerate some drought when mature.

Hardiness at least from USDA zone 5 through 10 with some occasional stem dieback in cold winters.

It is claimed:

1. A new cultivar of winter-hardy butterfly bush, *Buddleia* plant named 'Pink Cascade II' as herein illustrated and described.

* * * * *